(12) United States Patent
Volodarsky et al.

(10) Patent No.: US 10,517,334 B1
(45) Date of Patent: Dec. 31, 2019

(54) PORTABLE ELECTRONIC VAPORIZING DEVICE

(71) Applicant: Puff Corporation, Los Angeles, CA (US)

(72) Inventors: Roger Volodarsky, Los Angeles, CA (US); Avi Bajpai, Los Angeles, CA (US); Roger Sayre, Los Angeles, CA (US); Justin Cohen, Bloomfield, NJ (US)

(73) Assignee: PUFF CORPORATION, Los Angeles, CA (US)

( * ) Notice: Subject to any disclaimer, the term of this patent is extended or adjusted under 35 U.S.C. 154(b) by 0 days.

(21) Appl. No.: 16/373,170

(22) Filed: Apr. 2, 2019

Related U.S. Application Data

(63) Continuation of application No. PCT/US2019/013501, filed on Jan. 14, 2019.

(60) Provisional application No. 62/792,202, filed on Jan. 14, 2019.

(51) Int. Cl.
| | | |
|---|---|---|
| *A24F 47/00* | (2006.01) | |
| *A61M 15/00* | (2006.01) | |
| *A61M 15/06* | (2006.01) | |
| *A61M 11/04* | (2006.01) | |

(52) U.S. Cl.
CPC ......... *A24F 47/008* (2013.01); *A24B 15/167* (2016.11); *A61M 15/0021* (2014.02); *A61M 11/042* (2014.02); *A61M 15/06* (2013.01); *A61M 2205/8206* (2013.01)

(58) Field of Classification Search
CPC ..................................... A24F 47/008
See application file for complete search history.

(56) References Cited

U.S. PATENT DOCUMENTS

| | | | |
|---|---|---|---|
| 10,321,714 B1* | 6/2019 | Kane ............ | A24F 47/008 |
| 2009/0071481 A1 | 3/2009 | Fishman | |
| 2013/0319437 A1* | 12/2013 | Liu ............... | A24F 1/30 131/329 |
| 2014/0083441 A1* | 3/2014 | Kaplani ......... | A24F 47/008 131/329 |
| 2015/0122275 A1* | 5/2015 | Wu ............... | A24F 1/30 131/329 |
| 2015/0165137 A1 | 6/2015 | Mullinger et al. | |
| 2016/0219937 A1 | 8/2016 | Rado | |
| 2016/0302486 A1* | 10/2016 | Eroch ............ | A24F 47/008 |
| 2016/0366936 A1* | 12/2016 | Liu ............... | A24F 47/008 |
| 2017/0055579 A1* | 3/2017 | Kuna ............ | A24F 47/008 |
| 2017/0055588 A1* | 3/2017 | Cameron ....... | H05B 3/44 |
| 2017/0079324 A1 | 3/2017 | Eksouzian | |
| 2017/0251718 A1* | 9/2017 | Armoush ....... | A24F 1/30 |
| 2018/0098569 A1 | 4/2018 | Martin | |
| 2018/0125115 A1* | 5/2018 | Mueller ......... | A24F 5/04 |
| 2018/0271150 A1* | 9/2018 | Sparklin ........ | A61M 11/041 |
| 2019/0174825 A1* | 6/2019 | Neuhaus ....... | A24F 47/008 |

(Continued)

OTHER PUBLICATIONS

Puff Co., Peak Atomizer Assembly posted on Instagram retrieved from www.instagram.com/p/BfMk5MKIBp1/ Feb. 14, 2018.

(Continued)

*Primary Examiner* — James Harvey

(74) *Attorney, Agent, or Firm* — Bryan Cave Leighton Paisner LLP

(57) ABSTRACT

The present invention relates to a portable electronic vaporizing device for use in the inhalation of vaporizable substances.

13 Claims, 15 Drawing Sheets

(56) References Cited

U.S. PATENT DOCUMENTS

2019/0307171 A1* 10/2019 Kane ............... B01F 7/0025
2019/0313692 A1* 10/2019 Jones ............... A24F 1/30

OTHER PUBLICATIONS

Puff Co., Peak Video posted on Instagram retrieved from www.instagram.com/p/Bd-oaEkFrXC/ Jan. 15, 2018.
Puff Co., Glass Attachment Video posted on Instagram retreived from www.instagram.com/p/Bd3DfMRIWLo/ Jan. 12, 2018.
Puff Co., Puffco Peak Case posted on Instagram retrieved from www.instagram.com/p/Bd027vflYzM/ Jan. 11, 2018.
Puff Co., Puffco Peak Video posted on Instagram retrieved from www.instagram.com/p/BdtMs4qIHnH/ Jan. 8, 2018.
Puff Co., Puffco Peak Hero Shot posted on Instagram retrieved from www.instagram.com/p/BdybEMAI_zX/ Jan. 10, 2018.
Dr. Dabbler, Vaporizers for sale, retrieved from https://web.archive.org/web/20170222202821/https://drdabbervaporizersforsale.weebly.com/ Feb. 22, 2017.
Dr. Dabbler, Boost: Black Edition retrieved from www.drdabber.com/products/boost-black-edition 2019.
Dr. Dabbler, Boost Black Edition retrieved from www.drdabber.com/collections/all/products/boost-black-edition 2019.
Source Vapes, web page for Atomizers, retrieved from www.sourcevapes.com 2019.
Source Vapes, web page for Atomizers, retrieved from www.sourcevapes.com/collections/atomizers Feb. 16, 2016.
Vapexhale, Give the gift of relaxation, retrieved from www.xhl3.com Nov. 27, 2017.
Vapexhale, web page for starter kits, retrieved from www.xhl3.com 2019.
Cloud V Enterprises, Cloud V Bubbler Options, retrieved from cloudvapes.com/vaporizers/portable-enail/cloudv-electro-portable-dab-rig 2019.
Cloud V Enterprises, Ultra Slim Design Vaporizers, retrieved from cloudvapes.com/store/ Jan. 21, 2013.
Cloud V Enterprises, Cloud V, retrieved from cloudvapes.com/store/ Feb. 22, 2016.
Dabado Vaporizers, web page for Dabado Bolt, retrieved from dabadovaporizers.com/collections/bolts 2019.
Dabado Vaporizers, web page for Dabado Bolt, retrieved from dabadovaporizers.com Jan. 1, 2016.
Kevin H., Focusvape Tourist Review—The Accidental Tourist, retrieved from vapesterdam.com/review/focusvape-tourist-review/ 2019.
Focus Vape, web page of vaporizers, retrieved from focusvape.eu/shop/ Jul. 17, 2017.
PAX Labs, Inc., web page of vaporizers, retrieved from www.paxvapor.com Feb. 25, 2015.
PAX Labs, Inc., PAX 3, retrieved from paxvapor.com 2019.
Tarantola, A., The Puffco Peak vaporizer is a quick hit of concentrated genius, Engadget, retreived from /www.engadget.com/2018/03/16/puffco-peak-vaporizer-hands-on/ Mar. 16, 2018.
Koerber, B., This weed company just made a smart bong and it's awesome, Mashable, retrieved from mashable.com/2018/01/08/puffco-peak-smart-bong-dab-rig-concentrates/#8xqfBBSqkaqQ Jan. 8, 2018.
Waxxim, Vape Pen Bubblers shopping page, retrieved from www.waxxim.com 2019.
Engadget, Hands on Peak, retrieved from web.archive.org/web/20180330221034/https://www.engadget.com/2018/03/16/puffco-peak-vaporizer-hands-on/ Mar. 31, 2018.
Puff Co., Reservations are now open for Peak Atomizer Assembly, retrieved from web.archive.org/web/20180224162936/https://www.puffco.com/ Feb. 24, 2018.
Puff Co., Introducing the Peak, retrieved from vimeo.com/257080728 Feb. 28, 2018.
Patent Cooperation Treaty, International Search Report for PCT/US2019/013501, 6 pages Oct. 10, 2019.

* cited by examiner

PORTABLE ELECTRONIC VAPORIZING DEVICE

CROSS REFERENCE TO RELATED APPLICATIONS

This application claims the benefit of priority from U.S. Provisional Patent Application 62/792,202 filed on Jan. 14, 2019 and claims the benefit of International Application PCT/US19/13501 filed on Jan. 14, 2019. The disclosures of each of which are hereby incorporated herein by reference in their entireties.

FIELD OF THE INVENTION

Aspects of the present invention relate to portable electronic vaporizing devices for use with vaporizable products.

BACKGROUND

Electronic vaporizers are common place and are generally utilized for the purpose of aroma and/or inhalation therapy. In this regard, vaporizers heat a substance, herbs for example, such as tobacco, cannabis, lavender, chamomile, and many other types of plant material. The vaporizer may work by heating the substance through the use of direct heat or the use of hot air. There are three common ways of heating the substance. The first is thermal conduction where the substance is set directly on a heating element such as a ceramic or metal plate. The second is thermal radiation in which light is used to heat the substance. The third is convection where hot air is passed over the substance.

At lower levels of heat, vapors extracted from substances such as vegetable materials are mainly aroma therapeutic (inactive fragrance) and do not usually contain the active ingredients of the substance. Without the active ingredients being present, there is no physiological reaction. At higher levels of heat, active ingredients will be increasingly included in the vapor given off during heating. Usually, aromatic vapors have already been released and are not always present at the higher heat levels. With some substances, such as cannabis, active ingredients appear at different levels of heat.

After the substance is heated a mist or vapor containing some aspect of the substance is released and either enjoyed as an aromatic or inhaled to obtain a physiological reaction. The warm air containing the substance product can be harsh on the throat and bronchial tubes. Accordingly, some vaporizers use a cooling down process that allows water moisture to be included in the vapor produced. These vaporizers enable the user to inhale a cool moist vapor that is relatively less harsh and irritating. Vaporizers are often preferred over traditional methods of heating or smoking substances due to the reduction of harsh side effects. Some of these side effects include inhalation of tar, carbon monoxide, and other carcinogens either directly or from second hand smoke. With many states imposing smoking bans in public areas, vaporizers have become popular substitutes.

Accordingly, there is a need for improved vaporizers that provide an enhanced vaporizing experience, including vaporizers with improved quality of the vapor produced for inhalation and improved ease of use.

SUMMARY

Aspects of the invention are directed to a portable electronic vaporizing device comprising:

a base having comprising a gas flow path conduit therein, the gas flow path conduit comprising a conduit inlet and a conduit outlet;

a mouthpiece that is removably attachable to the base, the mouthpiece comprising:
   a mouthpiece housing comprising one or more mouthpiece walls at least partly defining a mouthpiece internal flow path through the mouthpiece housing;
   an inhalation outlet formed in a region of the one or more mouthpiece walls; and
   at least one mouthpiece inlet capable of being placed in communication with the conduit outlet of the base upon attachment of the mouthpiece to the base, to receive a flow of gas into the mouthpiece from the base; and an atomizer that is removably attachable to the base, the atomizer comprising:
   an atomizer inlet configured to receive a flow of gas into the atomizer;
   an atomizer housing comprising one or more atomizer housing walls that at least partially define an atomizer internal flow path therein,
   a container within the atomizer housing that is capable of holding a vaporizable product,
   a heating element capable of heating the vaporizable product held in the container,
   a first container inlet capable of introducing gas into the container to entrain vaporizable product;
   one or more second container outlets capable of flowing the gas having the vaporizable product entrained therein into atomizer internal flow path;
   one or more atomizer outlets capable of receiving the flows of gas from the atomizer internal flow path, and providing the flow of gas to the conduit inlet of the base, wherein the flow of gas having the vaporizable product entrained therein flows from the atomizer internal flow path and through the gas flow conduit inlet of the base to the mouthpiece inlet, and along the mouthpiece internal flow path to the inhalation outlet.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Aspects of the invention as described herein are directed to an improved portable electronic vaporizing device for the inhalation of vaporizable substances, such as aromatic substances, therapeutic substances and/or substances with physiological effects. Examples of such substances can include herbs, such as tobacco, cannabis, lavender, chamomile, and other types of plant material. In one embodiment, a vaporizable substance can comprise a cannabinoid, such as for example one or more of cannabadiol (a generally non-psychoactive therapeutic substance) and tetrahydrocannabinol (THC) (a psychoactive therapeutic substance). The vaporizable substance may in some embodiments be in the form of an oil and/or wax product comprising the vaporizable substance, e.g., as extracted from plant material containing the substance, and may optionally be provided in combination with carriers or other additives.

Figure 1:
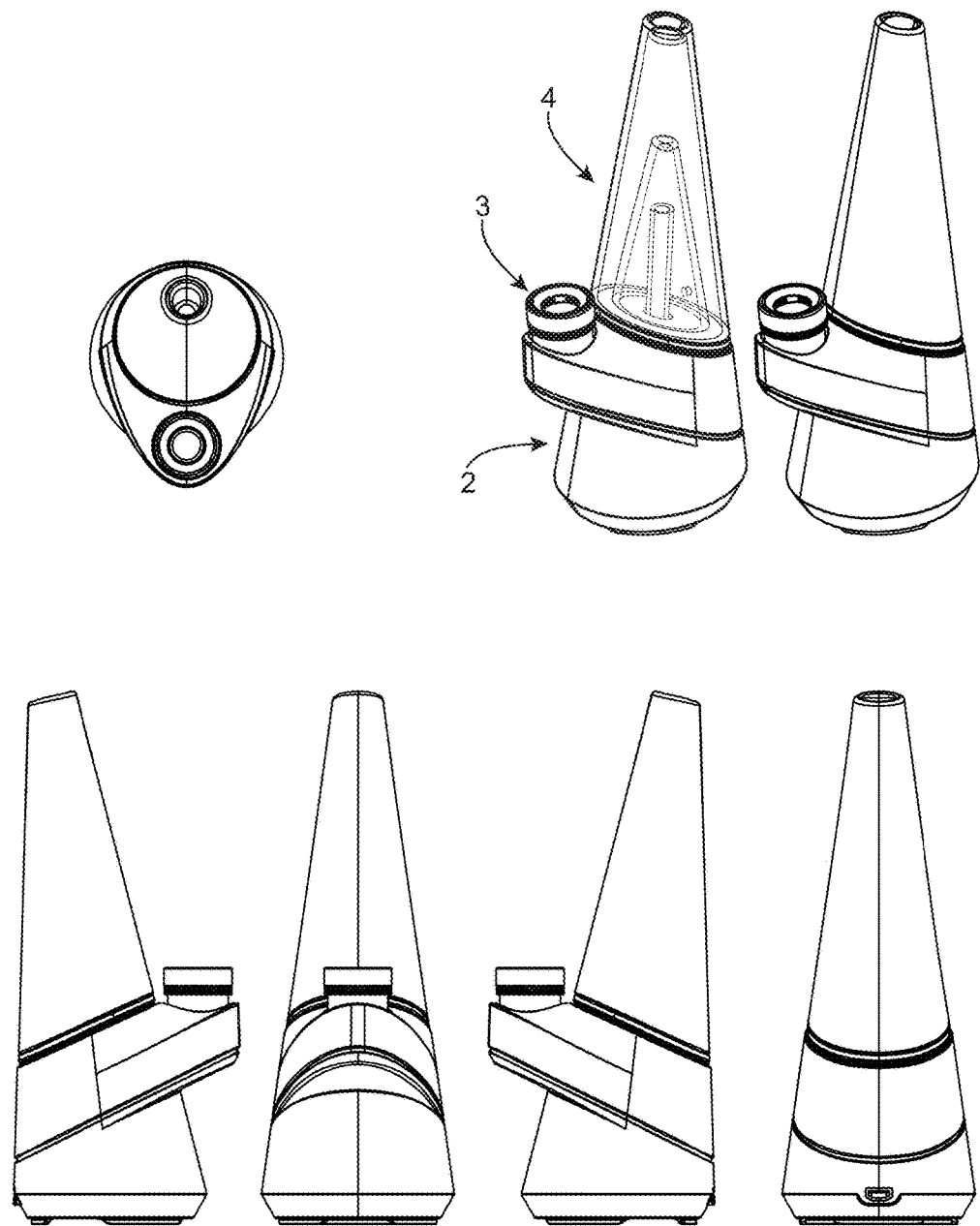
FIG. 1 shows embodiments of a portable electronic vaporizing device comprising a base, atomizer and mouthpiece.

Referring to FIG. 1, an embodiment of a portable electronic vaporizing device 1 is shown according to aspects of the disclosure herein. The portable electronic device 1 comprises a base 2, and atomizer 3 and a mouthpiece 4. The atomizer 3 is configured to receive a vaporizable product therein and to heat the vaporizable product to form a vapor therefrom. The mouthpiece 4 comprises an outlet where a user can inhale the vapor produced by the atomizer, optionally with water or other substances entrained therein. The base 2 provides a gas flow connection between the atomizer 3 and mouthpiece 4, to deliver the vaporized product from the atomizer 3 to the mouthpiece 4 for delivery to the use via inhalation thereof. The base 2 can also comprise a housing for one or more components for powering and/or controlling the device 1. For example, the base may contain compartments therein for storing a power source, such as a battery, for powering elements of the device 1 such as a heating element used in the atomizer 3. In a case where the device is powered by a rechargeable battery, such as a lithium ion battery, the base 2 may also comprise a charging port connectable to a battery charger (not shown). The base may also have compartment doors to allow access to a battery or other components held within the housing. The base 2 may also house further control circuitry for controlling the device, such as to provide predetermined heating cycles or heating programs, and may also allow for user interaction with the device via control buttons and/or control interface, a display and/or lights to signal to the user, and/or other control and operation features.

Figure 2:
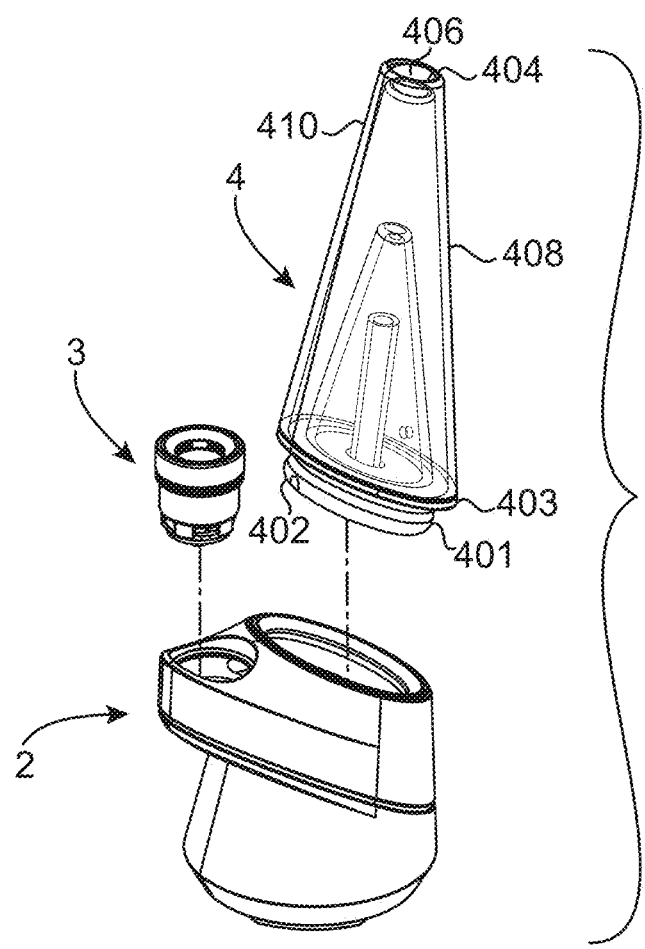
FIG. 2 is an exploded view of the device of FIG. 1.

Referring to FIG. 2, an embodiment of the device 1 is shown in exploded view, with the mouthpiece 4 and atomizer 3 removed from the base 2. In one embodiment, the mouthpiece 4 is removably attachable to the base 2, for example so as to allow a user to readily remove the mouthpiece for cleaning and/or replacement, as is described in further detail herein. In yet another embodiment, the atomizer may be removably attachable to the base, for example so as to allow a user to replace the atomizer 3 when no longer serviceable, for cleaning of the atomizer, and/or to more readily allow access to a container (e.g. bowl) where a vaporizable product may be loaded into the atomizer 3. In one embodiment, both the atomizer 3 and the mouthpiece 4 may be removably attachable to the base 2. In yet another version, the atomizer 3 may be independently removable from the base 2. That is, the atomizer 3 may be configured to be removably attached to the base such that it can be removed therefrom, without requiring that the mouthpiece 2 be removed beforehand. Referring to FIG. 2 it can be seen that the atomizer 3 itself is external to the mouthpiece 4, and its connection to the base 2 is also at a position that is outside the mouthpiece 4, such that the atomizer 3 can be removed from the base 2 while the mouthpiece is kept attached to the base. Similarly, according to the embodiment as shown, the mouthpiece 4 can be removed from the base 2 independently of the atomizer 3, as the mouthpiece 4 and its connection to the base are external to the atomizer, and so the mouthpiece 4 can be removed from the base 2 without requiring removal of the atomizer 3. Furthermore, in the embodiment as shown in FIG. 2, the atomizer 3 can be loaded with vaporizable product without requiring removal of the mouthpiece 4, and without requiring passing of the vaporizable product through a portion of the mouthpiece, as the atomizer can be accessed separately from the mouthpiece.

Figure 3:
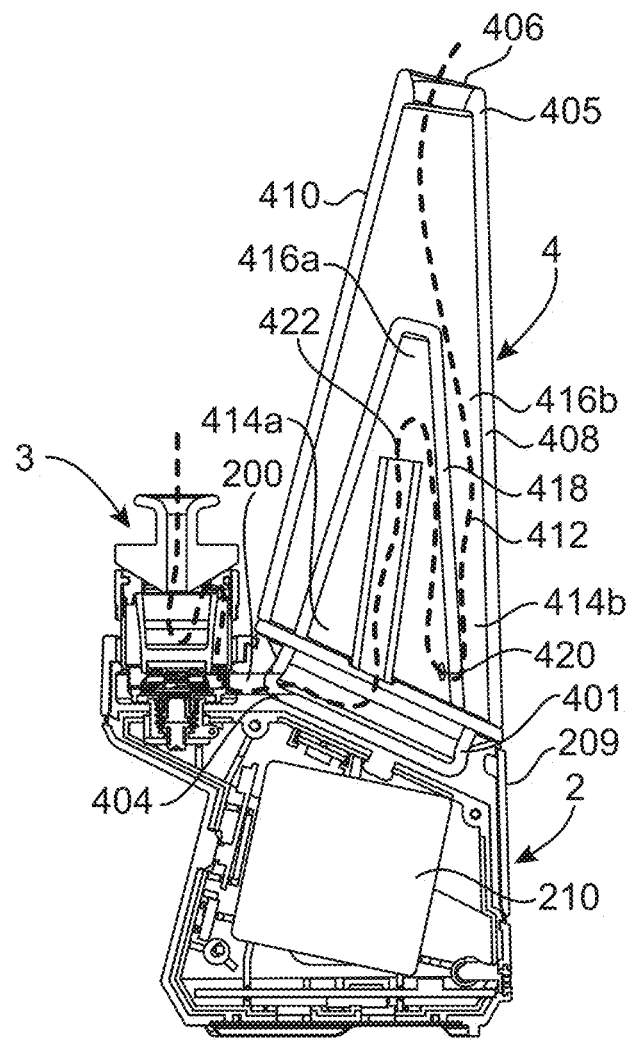
FIG. 3 is a schematic view of the device of FIG. 1.

Referring to FIG. 3, an embodiment of a gas flow path through the portable electronic device 1 is shown. In one embodiment, a flow of ambient air is received in the atomizer 3, where the ambient air is entrained with vaporizable product that is vaporized in the atomizer via a heating element. The gas comprising the ambient air and vaporizable product flows from the atomizer 3 to a portion of the base 2 having a gas flow conduit therein, and which provide a sealed gas flow connection between the atomizer 3 and mouthpiece 4. The gas received into the mouthpiece 4, where it is directed to an inhalation outlet of the mouthpiece, where the gas comprising the vaporizable product can be inhaled by the user. In one embodiment, water is provided a region of the mouthpiece 4 such that water is entrained with the gas passing through the mouthpiece, thereby providing a more pleasant inhalation experience to the user. An embodiment of an overall flow path of gas through the device 1 is depicted via dashed lines in FIG. 3.

Referring to FIGS. 4A-4D, embodiments of the base 2, and mechanism of attachment of the base 2 to one or more of the atomizer 3 and mouthpiece 4 are described in more detail. As shown in FIGS. 4A-4D, the base 2 comprising a gas flow path conduit 200 therein, the gas flow path conduit 200 comprising a conduit inlet 201a and a conduit outlet 201b, an embodiment of which may also be viewed with respect to FIG. 5. The conduit inlet 201a receives gas exhausted from the atomizer 3, and provides a flow of gas to the mouthpiece 4. In one embodiment, one or more airtight seals are formed between the base 2 and/or the atomizer 3 and mouthpiece 4, so as to create an airtight gas flow path between from the atomizer, through the gas flow path conduit 200 in the base 2, and to the mouthpiece 4. In the embodiment as shown, the gas flow conduit 200 in the base separates an atomizer internal gas flow path from a mouthpiece internal flow path.

According to one embodiment, the atomizer 3 and/or mouthpiece 4 are removably attachable to the base 2 via a fastening feature 202 that allows for repeated removal and re-insertion of the atomizer 3 and/or mouthpiece 4 into the base. In one embodiment, the fastening feature 202 may be located on the base 2, and/or the fastening feature 202 may be located on one or more of the atomizer 3 and mouthpiece, and/or the components may have mutually complementary fastening features that allow for repeatable removal and re-attachment of the atomizer 3 and/or mouthpiece 4 to the base 2.

In the embodiment as shown in FIGS. 4A-4D, the base 2 comprises first and second recessed regions 203a and 203b, comprising cavities formed in the base 2 that are configured to receive at least a portion of the atomizer 3 and mouthpiece therein. For example, the base can comprise a first recessed region 203a configured to receive at least a portion of the atomizer 3 therein, and a second recessed region 203b configured to receive at least a portion of the mouthpiece 4 therein. In one embodiment, the fastening feature 202 is provided as part of the base, and can comprise one or more airtight sealing members 204a, 204b located in the base, such as a first airtight sealing member 204a provided in the first recessed region to retain the atomizer therein, and/or a second airtight sealing member 204b provided in the second recessed region to retain the mouthpiece 4 therein. In yet another embodiment, the fastening feature 202 may be provided on the atomizer and/or mouthpiece. For example, the mouthpiece 4 may comprise a snap region 401 that is configured to be received by the second recessed region of the base, and that comprising a fastening feature 202 thereon to retain the step region in the base, as is described in more detail hereinbelow. In one embodiment, the fastening feature that removably retains one or more of the atomizer and/or mouthpiece in their respective recessed region is also capable of providing an airtight seal between the base and atomizer and/or mouthpiece. In another embodiment, the fastening feature comprises a structural element that is separate from and/or provided in addition to an airtight sealing member. For example, in one embodiment, the base and atomizer and/or mouthpiece may be fastened together by a fastening feature that does not provide an airtight seal, but an airtight sealing member may be provided about the gas flow interfaces of the base, such as about one or more of the base conduit inlet 201a and conduit outlet 201b, to provide an airtight connection for gas flowing from the atomizer through the base conduit and into the mouthpiece 4. According to yet another embodiment, the device comprises both fastening elements that provide an airtight seal, as well as further airtight sealing members along the gas flow path to ensure an airtight airflow. For example, referring to FIG. 4B, an airtight sealing member 204c can be provided about the gas conduit outlet 201b to provide an airtight connection to the mouthpiece inlet.

Figure 5:
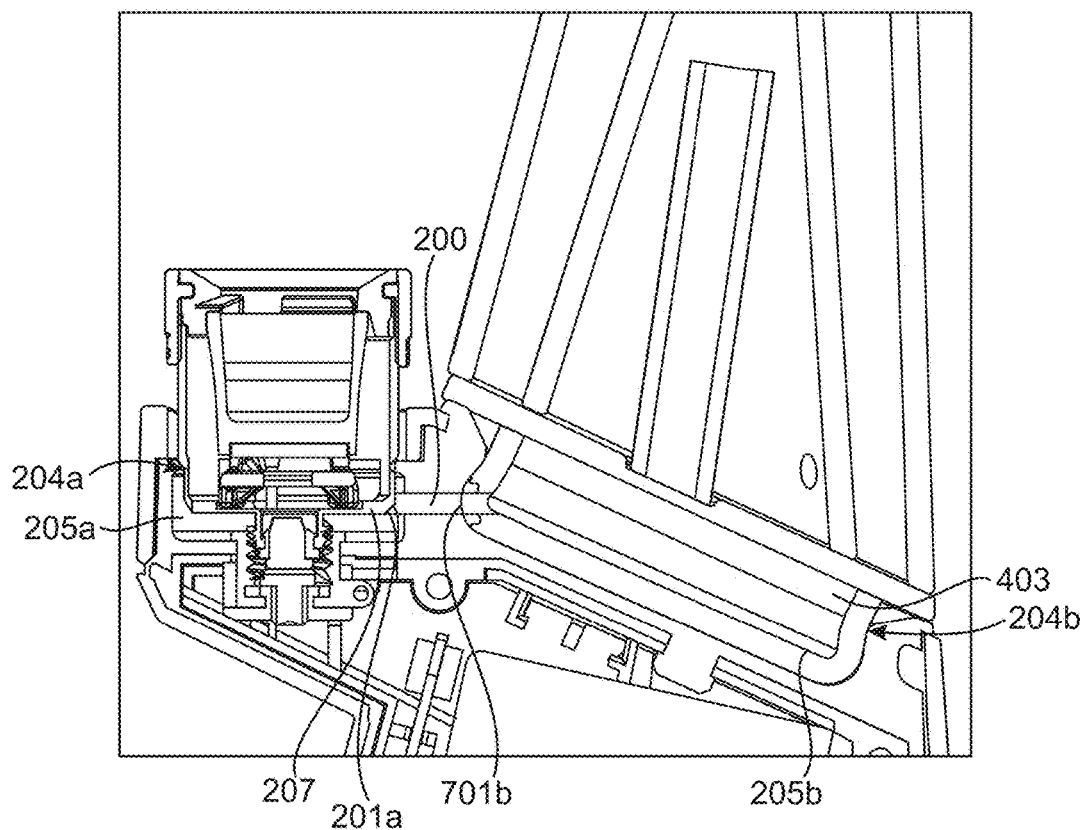
FIG. 5 shows a close-up schematic view of the device of FIG. 1

In one embodiment, the base 2 is capable of forming a first airtight compartment 205a via airtight seal with the atomizer, and/or is capable of forming a second airtight compartment 205b via an airtight seal with the mouthpiece 4, as shown in FIG. 5. In one embodiment, the base comprises a first recessed receiving region 203a formed therein that is configured to receive the atomizer 3, the first recessed receiving region 203a comprising an annular sealing region 204a provided about an internal circumference 206a of the first recessed receiving region, to form the airtight compartment between the base and atomizer in the portion of the first recessed region below the annular sealing region. In another embodiment, the base comprises a second recessed receiving region 203b formed therein that is configured to receive the mouthpiece, the second recessed receiving region 203b comprising an annular sealing region 204b provided about an internal circumference 206b of the second recessed receiving region, to form the airtight compartment between the base and mouthpiece in the portion of the second recessed region below the annular sealing region. In another embodiment, the base comprises a first recessed receiving region 203a formed therein that is configured to receive the atomizer, and a second recessed region 203b formed therein that is configured to receive the mouthpiece, and wherein at least one of the atomizer and/or mouthpiece comprise an annular sealing region provided about an external circumference thereof, to form an airtight compartment between the base and atomizer and/or mouthpiece in the portion of the first and/or second recessed regions below the annular sealing region 204a, 204b. In another embodiment, the base comprises a second recessed region 203b formed therein that is configured to receive the mouthpiece, and wherein a sealing region is provided on one or more of the base and/or mouthpiece about one or more of the gas flow path conduit outlet on the base and/or the at least one mouthpiece inlet on the mouthpiece, to form an airtight seal between the gas flow conduit outlet and the mouthpiece inlet. Furthermore, in one embodiment at least a portion of the first airtight compartment in the first recessed region 203a forms a passage 207 for flow of gas from the atomizer to the gas flow path conduit in the base, below the annular sealing region, as shown in FIG. 5.

In one embodiment, an annular sealing region provided about a recessed cavity in the base, and/or about a circumference of the atomizer and/or mouthpiece, comprises an elastomeric, rubber and/or silicone material. In another embodiment, the base 2 comprises one or more elastomeric, rubber and/or silicone sleeves 208 conformally lining one or more recessed regions 203a,203b, and/or the conduit 200. In one embodiment, the sleeve 208 may be a single sleeve piece lining at least a portion of the recessed regions 203a, 203 and conduit. According to yet another embodiment, at least one of the atomizer and mouthpiece can comprise an elastomeric, rubber and/or silicone sleeve conformally lining at least a part of a surface thereof that is received by first and/or second recessed regions of the base. In yet another embodiment, the sleeve 208 provided in one or more of the recessed regions 203a, 203b comprises one or more annular protrusions extending therefrom, such as by molding of the sleeve material to form the protrusions, which can serve as airtight sealing members 204a, 204b between the base and atomizer and/or mouthpiece.

In one embodiment, the base 2 comprises a second recessed receiving region 203b formed therein that is configured to receive the snap region 401 of the mouthpiece 4, the second recessed receiving region comprising the annular sealing region 204b provided about an internal circumference thereof, to form an airtight compartment between the base and snap region of the mouthpiece in the portion of the second recessed region below the annular sealing region. In yet another embodiment, the second recessed receiving region further comprises the annular sealing region 204c about the conduit outlet 201b to form an airtight seal between the conduit outlet 201b and a mouthpiece inlet 402. In one embodiment, the gas flow path conduit outlet 201b in the base is located below the annular sealing region 204b in the second recessed region, such that an interface between the gas flow path conduit outlet in the base, and the mouthpiece inlet is located in an airtight compartment portion of the second recessed receiving region. In one embodiment, the annular sealing region 204b, 204c comprises at least one of a rubber, elastomeric, and a silicone material. In yet another embodiment, the second recessed region is sized an shaped to accommodate a snap region 401 of the mouthpiece that comprises an annular indentation 403 formed about a circumference of the mouthpiece towards a bottom end 404 of the mouthpiece that is distal to an inhalation outlet 406 of the mouthpiece, the annular indentation being configured to conformally mate with the annular sealing member in the second recessed region to so as to form the airtight compartment.

As described above, in one embodiment the base 2 comprises a housing 209 that is configured to house a power source 210 for powering a heating element in the atomizer 2, and optionally comprises one or more control elements for operating components of the device 1. For example, in one embodiment the power source 210 can comprise a rechargeable battery, such as a lithium-ion battery. The housing may also contain outlets to connect the device with an electrical outlet and/or other devices, and may house control elements such a CPUs and/or wireless transmitters for controlling heating and vapor production with the device, either via direct or wireless input into the device by a user.

Referring to FIGS. 6A-6C and 7-11, an embodiment of an atomizer 3 is described. In the embodiment as shown, the atomizer 3 is removably attachable to the base, an includes an atomizer inlet 301 configured to receive a flow of gas into the atomizer 3, and an atomizer housing 10 comprising one or more atomizer housing walls 304 that at least partially define an atomizer internal flow path therein. The atomizer 2 is further configured to contain a container 7 (e.g., a bowl) within the atomizer housing 302 that is capable of holding a vaporizable product therein. The atomizer further comprises a heating element 8 capable of heating the vaporizable product held in the container 7. According to the embodiment as showing, the atomizer comprises a first container inlet 305 capable of introducing gas into the container 7 to entrain vaporizable product therein, and comprises one or more second container outlets 306 capable of flowing the gas having the vaporizable product entrained therein into an atomizer internal flow path 308. Embodiments of the atomizer 3 comprise one or more atomizer outlets 309 capable of receiving the flow of gas from the atomizer internal flow path 308, and providing the flow of gas to the conduit inlet 201a of the base 2.

According to one embodiment, the at least one heating element 8 is disposed within the atomizer housing 10. For example, the at least one heating element 8 may be disposed below a bottom surface 310 of the container 7 that is adapted to receive the vaporizable product therein. In one embodiment, the heating element comprises a ceramic heating plate, such as an alumina plate. The heating element 8 may be capable of resistively heating the container 7 via thermal contact therewith, as in direct contact with the bottom surface 310. In one embodiment, the heating element 8 is attached to conductive elements such as wires leading to the power source (e.g. battery) to provide an applied voltage for the resistive heating. In one embodiment, the container 7 adapted to receive and hold the vaporizable product comprises a thermally conductive ceramic material, such as alumina, such that placing the container is in thermal contact with the heating element causes heating of the container.

According to yet another embodiment, the atomizer 3 comprises a bottom insulating element 9 comprising a spacer disposed between the heating element 8 and atomizer housing 10 that thermally insulates the heating element 8 from the atomizer housing 8. The bottom insulating element 9 may also act to secure the heating element in position at a bottom end 312 of the container, such as in contact with the bottom surface of the container 7. In one embodiment, the bottom insulating element comprises a ceramic having a lower thermal conductivity than the container and/or heating element, so as to thermally isolate the container and/or heating element from the atomizer housing. For example, in one embodiment the bottom insulating element can comprise a thermal conductivity of less than 4 W/mk, less than 3.5 W/mk and/or less than 3 W/mk, whereas the container and/or heating element may comprise a thermal conductivity of at least 10 W/mk, at least 15 w/mk and/or at least 20 W/mk.

Figure 6A:
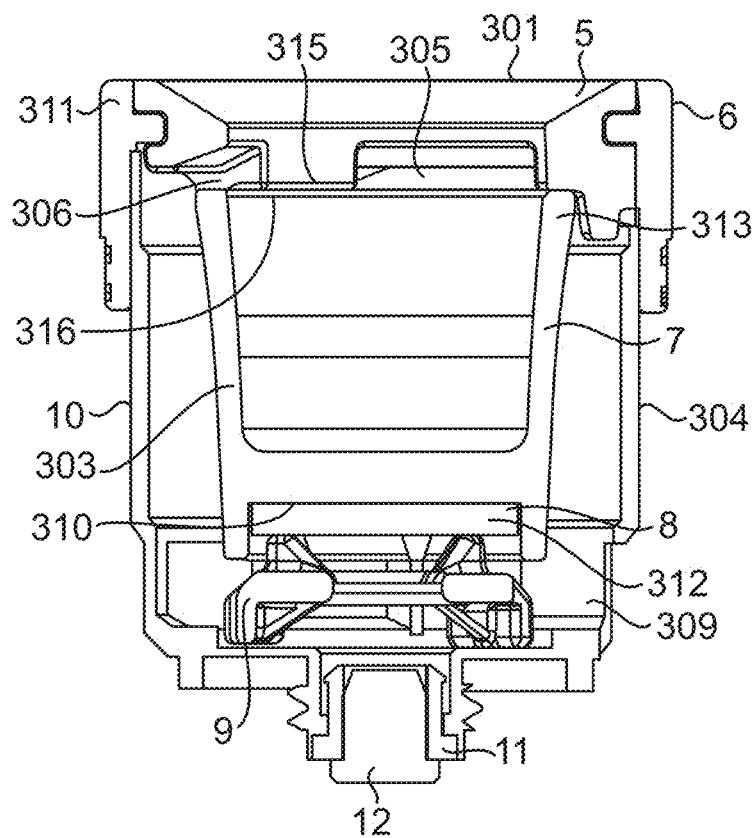
FIGS. 6A-6C show embodiments of an atomizer.

According to another embodiment, the atomizer 3 comprise a top insulating element 311 that thermally insulates a top end 313 of the container 7 from the atomizer housing 10. In one embodiment, the top insulating element 311 is configured to receive a carb cap 17 thereon. For example in one embodiment, the device 1 is configured to operate with a carb cap 17 positioned upstream of the atomizer 3, the carb cap comprising a stopper having a conduit 314 formed therein to provide a flow of ambient air into the atomizer 3. In one embodiment, the container 7 is thermally insulated from the atomizer housing 10 by both the bottom insulating element 9 that positions the container within the housing at a bottom end of the container, and the top insulating element 311 that positions a top end of the container in the housing. In one embodiment, referring to FIG. 6C, the top insulating element 311 comprises inner and outer annular insulating rings 5, 6. In one embodiment, an inner circumference of the inner annular insulating 5 ring defines the atomizer inlet 301, and is in communication with the first inlet 305 of the container 7. In the embodiment as shown in FIG. 6A, the atomizer inlet 301 is directly above the first inlet 305, and/or the atomizer inlet 301 and first container inlet may comprise the same inlet. That is, in one embodiment, the atomizer inlet may be aligned with and lead to a container inlet positioned below the inner annular ring 5 of the top insulating element 311.

In one embodiment, the atomizer 3 comprises an outer annular ring 6 that forms an annular jacket that is flush with the outer surface of the inner annular ring 5, and extends in an axial direction beyond the inner annular ring such that a portion of the interior surface of the outer annular ring is in contact with an outer surface of the atomizer housing 10. In one embodiment, the outer annular ring 6 may secure the inner annular ring 5 to the atomizer housing 10 via frictional forces and/or via a snap mechanism or other fastening mechanism between a portion of the interior surface of the outer annular ring and the outer surface of the atomizer housing. In one embodiment, the outer annular ring comprises an annular jacket that forms an airtight seal with the atomizer housing.

In one embodiment, one or more of the inner and outer annular rings 5, 6 are capable of thermally isolating the container 7 from the atomizer housing 10, by having a lower thermal conductivity. For example, one or more of the inner and outer annular insulating rings can comprise a thermal conductivity of less than 4 W/mk, less than 3.5 W/mk and/or less than 3 W/mk, whereas the container may comprise a thermal conductivity of at least 10 W/mk, at least 15 w/mk and/or at least 20 W/mk. IN one embodiment, a bottom surface 315 of the inner annular insulating ring 5 is in contact with an upper surface 316 of the container 7.

In one embodiment, one or more of the container 7 and/or thermally insulating element 311, such as the inner annular ring 5, comprise one or more apertures 318 therein that correspond to the one or more container second outlets 306. For example, in one embodiment the inner annular ring 5 comprises one or more indentations 320 formed in the bottom surface 315 thereof, such as about a circumference thereof, which form one or more apertures 318 between the bottom surface 315 of the inner annular ring 5 and the top surface 316 of the container 7. In yet another embodiment, the inner annular ring 5 comprises one or more apertures formed in the body thereof, such as about a circumference thereof, to provide the one or more container outlets. In yet another embodiment, the container itself comprises one or more apertures 318 formed in one or more walls thereof, wherein the one or more apertures comprise the one or more second container outlets 306. According to certain embodiments, first container inlet 305 introduces a gas flow received through the inner insulating annular ring 5 into the container 7, and the one or more second container outlets 306 flow gas out of the container through the one or more apertures 318. The second container outlets 306 may thus be a separate aperture and/or opening than the first container inlet 305, such that air comes through the inlet and passes through a separate outlet when exiting the container 7.

Furthermore, in one embodiment, the top insulating element 311 is removable from the atomizer housing 10 to allow access to the container 7. For example, the insulating element 311 may be removable by simply lifting or twisting the top insulating element form the atomizer housing 10. According to yet another embodiment, the atomizer housing 10 comprises a lower portion 322 that is threaded, and that may be complementary to a threaded socket in the first recessed region 203a of the base 2, so the atomizer can be screwed into the threaded socket of the base. In yet another embodiment a lower portion of the atomizer housing may connects to the base via a magnet, span mechanism or other fastening feature.

Figure 6B:
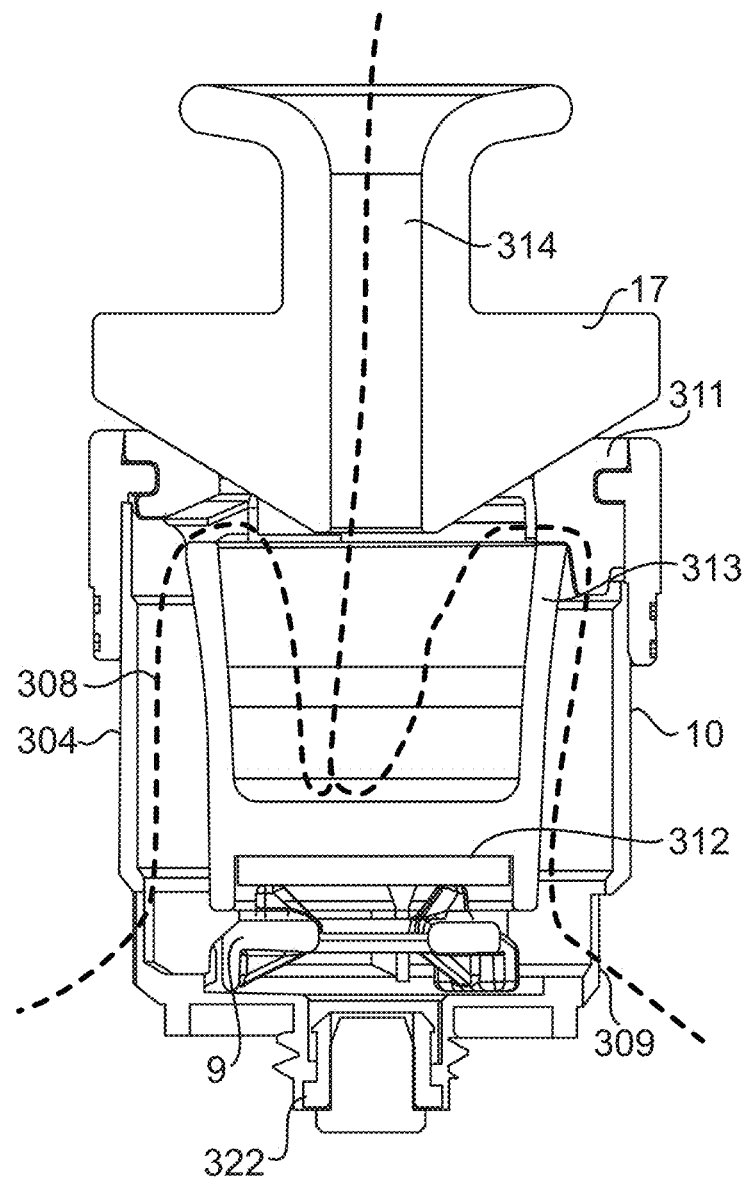
Figure 6C:
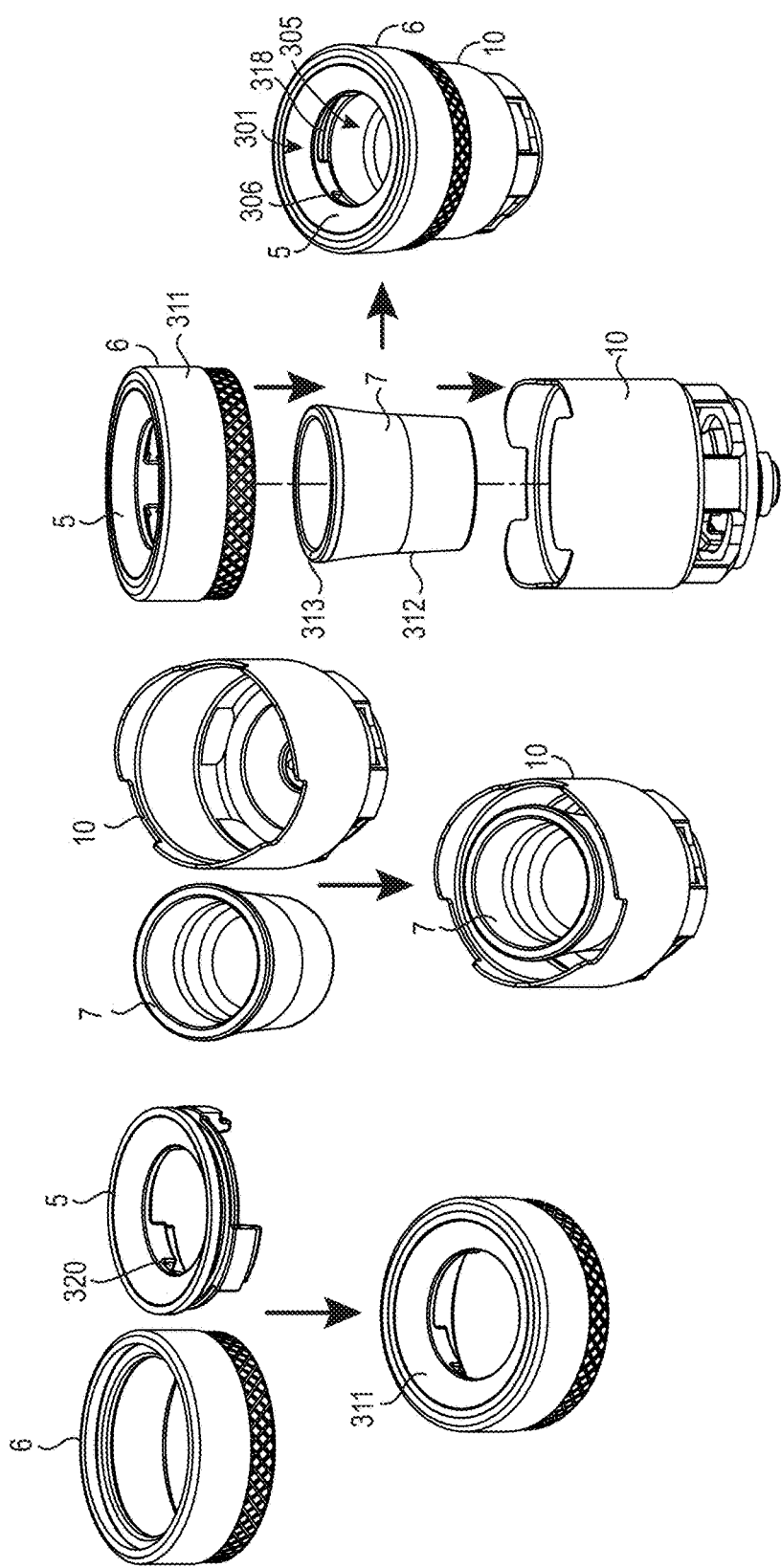
Figure 7:
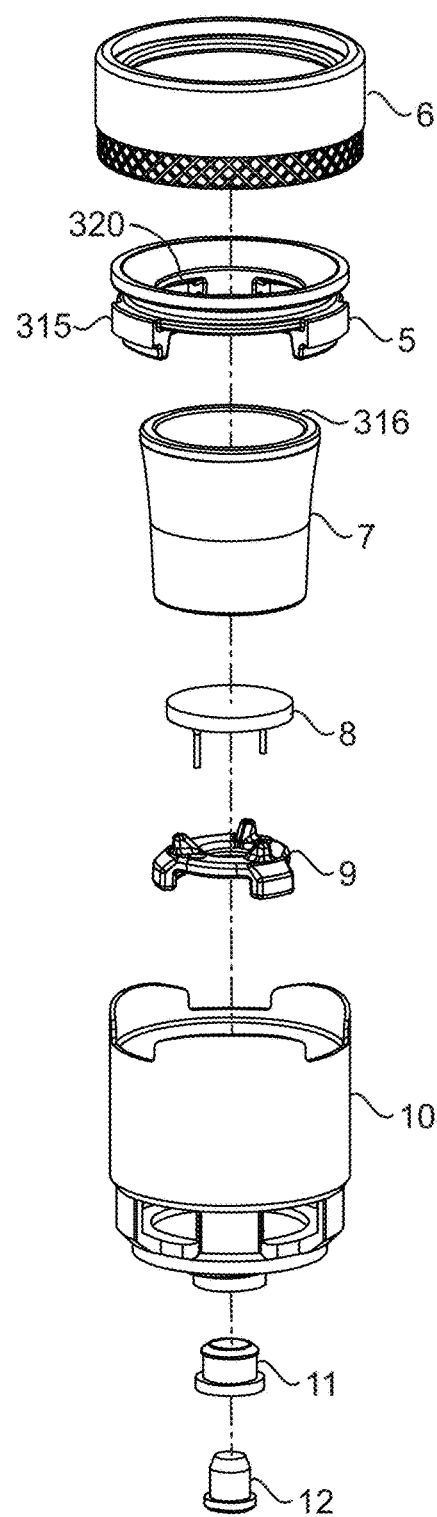
FIGS. 7-11 show views of embodiments of components of an atomizer.
Figure 8:
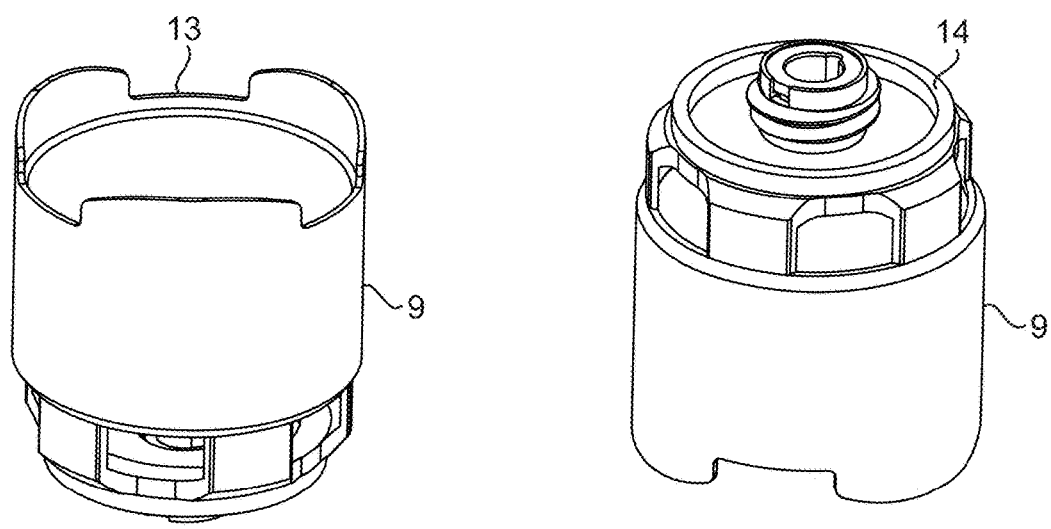
Figure 9:
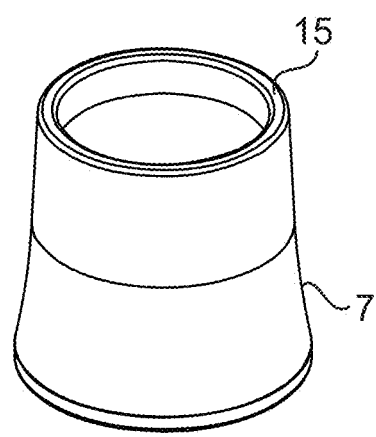
Figure 10:
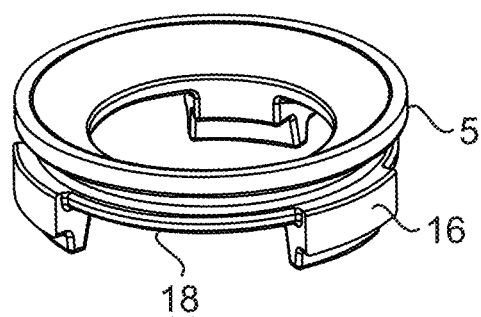
Figure 11:
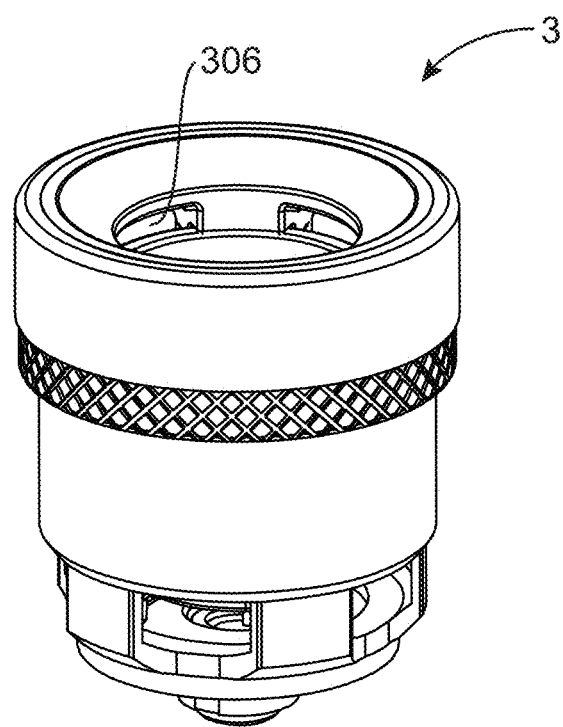

According to one embodiment, atomizer housing at least partially directs gas from the one or more second container gas outlets 306 along the internal atomizer gas flow path 308 (shown as a dashed line in FIG. 6B), in a passage 324 formed between walls of the container 7 and the atomizer housing 10. The atomizer housing 10 can comprises one or more apertures/outlets 309 formed therein to flow gas from the internal atomizer gas flow path 308 to the airtight passage 207 that is external to the atomizer housing in the first recessed region 203a of the base 2. In one embodiment, the atomizer housing apertures/outlets 309 are located at a lower end of the atomizer housing, and the atomizer housing 10 redirects flow of the gas from the one or more second container gas outlets 306 in a downward direction along a passage 324 formed between the housing walls and container walls, to the atomizer housing apertures/outlets 309. As shown in FIG. 6B, in one embodiment a flow of gas through the atomizer 8 comprises a flow through the first container inlet into a top of the container, flow out of the container through second container outlets that are separate from the inlet, and that are towards a top 313 of the container, flow downward between the atomizer housing and container wall towards a bottom of the atomizer and through apertures of the atomizer towards the bottom of the atomizer housing.

In one embodiment, the one or more second container outlets 306 are located radially externally to the first container inlet 305, and/or are positioned in an arrangement circumferentially surrounding the first container inlet 305. The second container outlets 306 may also be located towards a top end of the atomizer and/or container. In a further embodiment, the apertures and/or outlets 309 for exhausting gas from the atomizer are located below the first container inlet and/or second container outlet, towards a lower end of the atomizer.

Further embodiments of the atomizer are described herein. For example, in one embodiment, inside the atomizer housing 10, a container comprising a bowl 7 is positioned on top of the heating element 8, and may be made of a highly thermally conductive material, which can include ceramic, quartz, or metals, allowing efficient heat transfer. The heating element 8 and the bowl 7 are secured and insulated by the bottom insulating element 9 and top insulating element 311 respectively, these two elements firmly locating the heating element 8 and bowl 7 within the atomizer. These two elements are made with low thermally conductive, yet high heat withstanding, material so that minimal heat is lost from the heating element and bowl. The top insulating element comprises an outer annular ring comprising sleeve 6, made of an insulating material, like silicone or plastic. The sleeve 6 fastens to the housing 10 and makes an airtight seal while the inner annular ring 5 insulates and positions the bowl 7. The sleeve 6 may also protect the user from heat and serves as a grip for screwing and unscrewing the atomizer.

After extended use the bowl 7 may become dirty. Because the top insulating element comprising in inner annular ring 5 and sleeve (6) are removable, the bowl can be taken out and easily cleaned. When the sleeve and top insulating element are assembled on the atomizer housing the bowl is held in place and a sealed airpath is formed. Air may enters the top of the bowl through a carb cap 17. The carb cap 17 may be capable of directing high velocity air to the bottom of the bowl, where the material is vaporized. Air then exits the top of the bowl as vapor through the second outlets which are apertures in the inner annular ring (5) above the bowl. These slots/apertures could also be cut into the top of the bowl The vapor travels through the slots in the inner annular ring and down a gap formed between the bowl and the atomizer housing. The vapor can leaves the bottom of the atomizer and travels through an airpath into the mouthpiece. FIG. 6B shows a cross sectional view of the assembled atomizer with the carb cap and illustrates the airflow through the atomizer, entering through the carb cap and exiting out of the bottom of the atomizer.

In certain embodiments, material that leaks out of the bowl 7 can seep down into the bottom of the atomizer near the connection point. Accordingly, it may be important for this area to be sealed so that the leaking material does not inhibit the passing of the current from power source to heating element. This seal is provided by the electrode insulator 11 which holds the electrode 12. The electrode insulator secures and holds separately the electrode from the housing. One lead wire of heating element 8 can be held between the insulator and the housing 10, the other lead wire can be held between the insulator and the electrode, therefore a current path in and out of the heating element can be created. There can be also grooves cut into the atomizer housing to position these lead wires. The electrode insulator can press the wires into these grooves and make a water and airtight seal against the housing and electrode which may prevents leaking. In certain embodiments, material may also leak out of the bottom of the atomizer through the air cuts in the housing 10. Accordingly, it may be important that this material does not reach the connection point on the atomizer or the power source. When the atomizer is connected to the base, a rib 14 running around the bottom of the atomizer housing 10 can create a seal. This seal can creates a separation between the air holes and connection point and may prevent any material from reaching the electrical connection points on the atomizer or base.

Furthermore, because the bowl 7, heating element 8 and inner annular ring 5 may interact with sticky material during use, there is a chance for them to become stuck together. In certain embodiments, if the bowl is twisted during use, for example while the user is tightening or untightening the atomizer by gripping the sleeve, the heating element could be twisted and could lead to subsequent breaking of its lead wires. Accordingly, features may be included in the atomizer housing 10 and inner annular ring 5. For example, slots in the atomizer housing 10 may line up with embossed features 16 in the inner annular ring 5, so that the two lock together and cannot be twisted independently. This protects the heating element from damage when tightening or loosening the atomizer from the base.

In one embodiment, the bowl itself can include a rib 15 around its bottom face, which is the face that interacts with the heating element. This rib may have three functions, it can positions the bowl, cover the heating element, and/or minimize heat loss, and it can shroud the heating element from debris. The debris could be water or liquid material that leaks down into the heating elements environment. Since the heating element may operate at a high temperature, a substance of room temperature contacting the heating element can result in significant thermal shock which could damage or permanently break the heating element. The rib on the bottom of the bowl blocks debris by creating a protective wall around the heating element.

Referring to FIGS. 1-3, 5 and 12, embodiments of the mouthpiece 4 are further described. In one embodiment, the mouthpiece 4 is removably attachable to the base 2. The mouthpiece can generally comprise a mouthpiece housing 408, comprising one or more mouthpiece walls 410 at least partly defining a mouthpiece internal flow path 412 through the mouthpiece housing (e.g., as shown in FIG. 3). The mouthpiece can further comprises the inhalation outlet 406 formed in a region of the one or more mouthpiece walls 410, such as towards a top end 405 of the mouthpiece 4. The mouthpiece can further comprise at least one mouthpiece inlet 402 capable of being placed in communication with the conduit outlet 201b of the base 2 upon attachment of the mouthpiece 4 to the base 2, to receive a flow of gas into the mouthpiece 4 from the base 2. In some embodiments a gas flowed through the mouthpiece from the mouthpiece inlet 402 to the inhalation outlet 406, may take a convoluted path through the interior volume of the mouthpiece and along the internal flow path, such as for example when a water filtering region is provided as part of the mouthpiece.

In one embodiment, the mouthpiece comprises a snap region 401 that is configured to removably attach the mouthpiece to the base. For example, in one embodiment, the base can comprises the second recessed receiving region 203b for receiving the mouthpiece therein via the snap region 401, which may be shaped and sized to fit within the second recesses receiving region. The snap region 401 may be located at the bottom end 404 of the mouthpiece, an in certain embodiments the mouthpiece inlet 402 may located in the snap region 401, of the mouthpiece. IN one embodiment, the second receiving region 403b may be at least partially lined with a rubber, silicone, and/or elastomeric sleeve to conformally mate the second recessed region with the snap region of the mouthpiece. In yet another embodiment, at least a portion of the snap region of the mouthpiece may be lined with a rubber, silicone, and/or elastomeric sleeve to conformally mate the second recessed region with the snap region of the mouthpiece. As yet another example, in one embodiment, the sleeve 208 comprises an annular sealing region 204b that protrudes inwardly from sidewalls of the second recessed region to contact and form an airtight seal with the mouthpiece.

In yet another embodiment, the mouthpiece comprises one or more a water filtering regions 414a, 414b, capable of holding a volume of water therein, the water filtering region being located along the mouthpiece internal flow path, such that water vapor becomes entrained into gas passing through water in the water filtering region. In the embodiment as shown in FIG. 3, a volume of water can be provided to partly fill in internal volume of the mouthpiece volume along a lower region of the internal mouthpiece volume.

In one embodiment, the at least one mouthpiece inlet 402 is located towards a bottom region 404 of the mouthpiece housing 408, and the inhalation outlet 406 is located distal to the at least one mouthpiece inlet 402 at an upper region 405 of the mouthpiece housing. According to yet another embodiment, the mouthpiece 4 comprises a plurality of chambers 416a, 416b that are connected to one another along the mouthpiece internal flow path 412. For example, the mouthpiece can comprise a first chamber 416a that is internal to a second chamber 416b, and wherein a flow of gas along the mouthpiece internal flow path 412 passes through the first chamber and into the second chamber. In one embodiment, the second chamber at least partially circumferentially surrounds the first chamber. In one embodiment, the mouthpiece comprises one or more internal walls 418 defining the first chamber 416a, and wherein the second chamber 416b is defined between the one or more internal walls 418 and the mouthpiece housing 408. In one embodiment, lower portions of the first and second chambers 416a, 416b comprise water filtering regions configured to receive and hold water therein. Furthermore, in one embodiment, the first and second chamber are connected to each other by at least one port 420 formed in the one or more internal walls 418.

In the embodiment as shown in FIG. 3, the first chamber 416a comprises a first chamber inlet 422 that is positioned above the at least one port 420 formed in the one or more internal walls, which port may be located at or below a level of water in the chambers when water is provided in the mouthpiece. In one embodiment, a flow of gas exiting the first chamber inlet 422 is directed by the one or more internal walls 418 towards the water filtering region in a lower portion of the first chamber 416a, and the gas exits the water filtering region in the lower portion of the first chamber 416a through the one or more ports 420 to enter a water filtering region of a lower portion of the second chamber 461b, and wherein gas having water vapor therein exits the water filtering region of the lower portion of the second chamber and is directed by the passage formed between the housing walls 410 and internal walls 418 to be output from the mouthpiece via the inhalation outlet. In the embodiment as shown in FIG. 3, the first chamber inlet 422 is at the end of a tube 424 extending upwardly into the first chamber 416a, the tube comprising an aperture to receive gas from the mouthpiece inlet, and wherein the first chamber inlet is located at a location that is higher than the port connecting the chambers. In another embodiment, the one or more internal walls 481 comprise a conically-shaped internal wall, and the mouthpiece housing comprises a conical housing wall about the conically-shaped internal wall.

In one embodiment, the mouthpiece 4 comprises a snap region 401 with one or more fastening features 202 on an external surface 426 thereof to fasten the snap region to the recessed region 203b of the base 2. In one embodiment, the fastening feature 202 may provide a sealing fit between the snap region and the recessed region when the snap region is inserted into the recessed region. In one embodiment, the fastening features may be able to removably fasten the mouthpiece to the base such that mouthpiece can withstand at least 2 lbs, at least 3 lbs and/or at least 5 lbs of vertical force before the snap region of the mouthpiece releases from the recessed region of the base.

In yet another embodiment, the at least one mouthpiece inlet 402 may direct gas into the mouthpiece in a direction that is not co-linear with and/or that is other than a direction that gas exits the mouthpiece via the inhalation outlet 406. For example, the at least one mouthpiece inlet may direct gas into the mouthpiece in a direction that is substantially perpendicular to a direction that gas exits the mouthpiece via the inhalation outlet.

Figure 12:
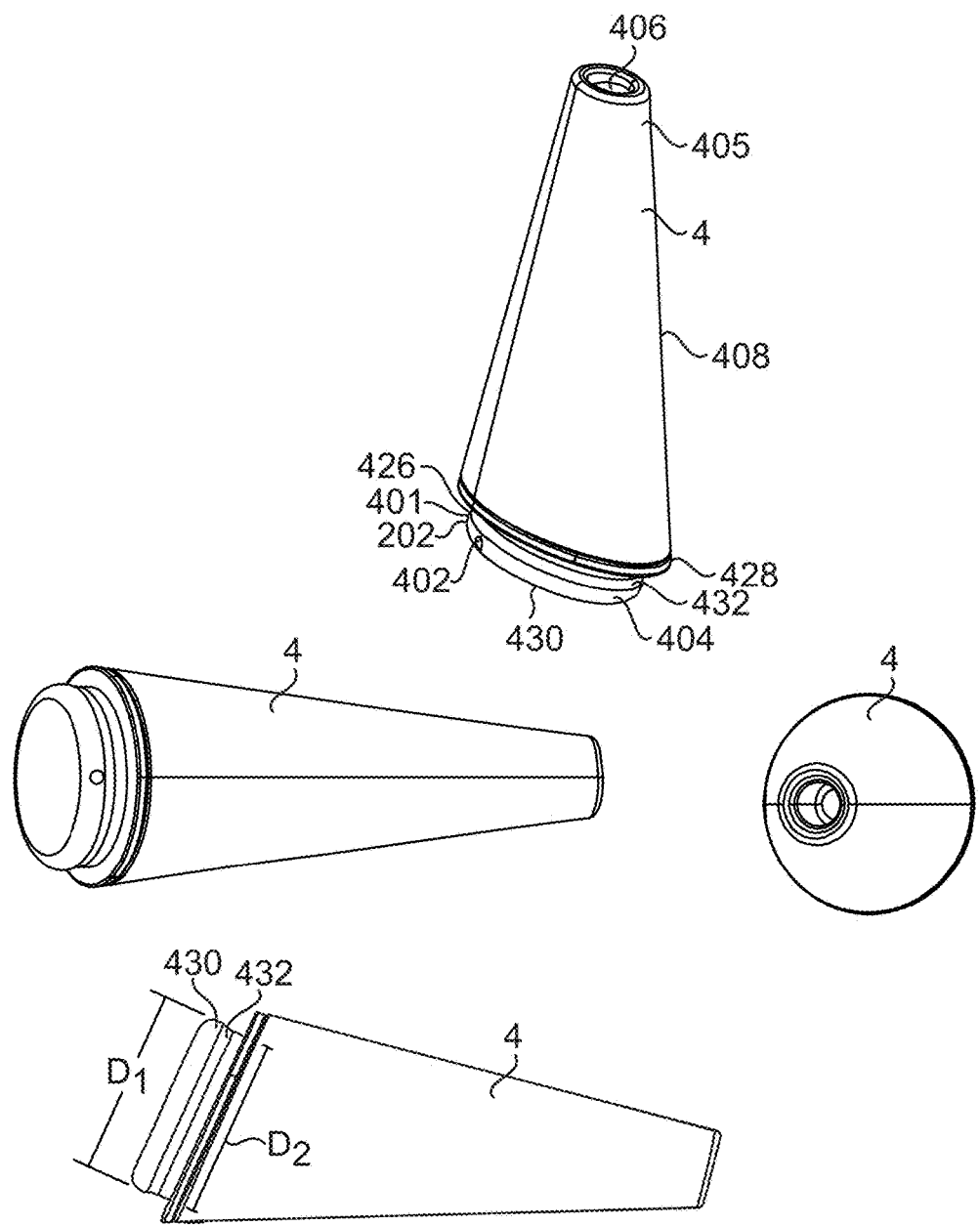
FIG. 12 shows views of embodiments of a mouthpiece.

In one embodiment, the at least a portion of the mouthpiece housing, and even the entire mouthpiece housing, may be formed of glass. In one embodiment, the snap region 401 of the mouthpiece may also be formed of glass. Internal structures such as internal walls between compartments, and tubes for introduction of gas, may also be formed of glass. In one embodiment, the snap region 401 of the mouthpiece comprise a greatest diameter $D_1$ (the largest diameter along the height of the snap region, see e.g. FIG. 12) that is at least 20 mm, at least 30 mm, and/or at least 50. In some embodiments, the snap region 401 may be considered to be that portion of the mouthpiece that is received by the recessed region of the base. As shown in FIG. 12, a body region 428 that is clear of the recessed region when the mouthpiece is connected to the base, may in some embodiments have a diameter that exceeds that of the snap region 401 that fits within the base. Furthermore, in one embodiment an internal volume of the mouthpiece 4 is configured to accept at least 1 fluid ounces of water therein during operation a device comprising the mouthpiece.

Figure 4A:
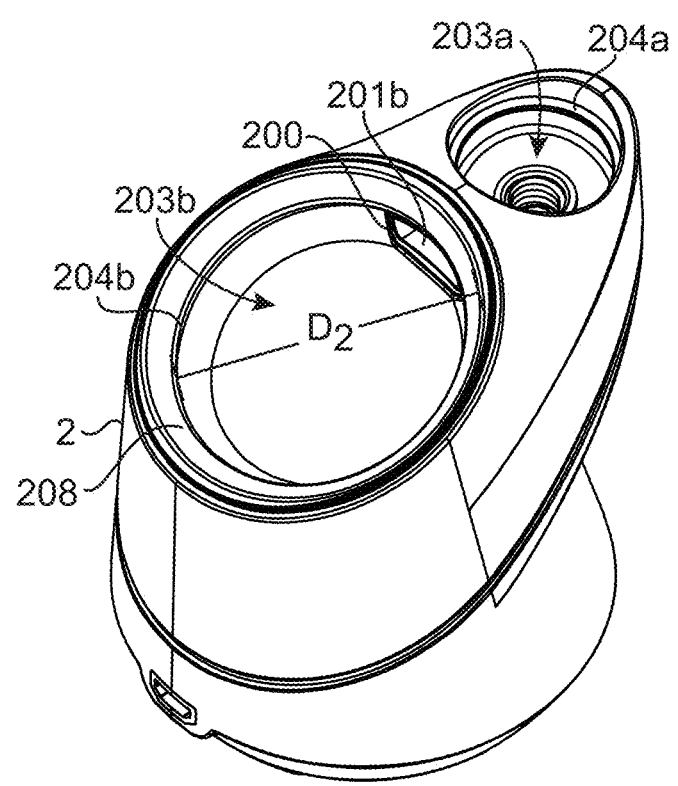
FIGS. 4A-4D shows an embodiment of a base.
Figure 4B:
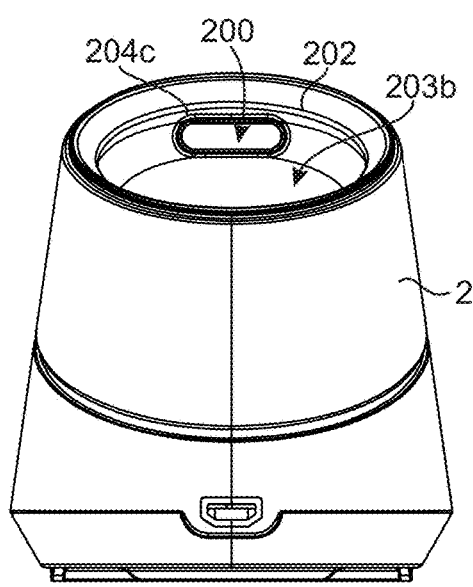
Figure 4C:
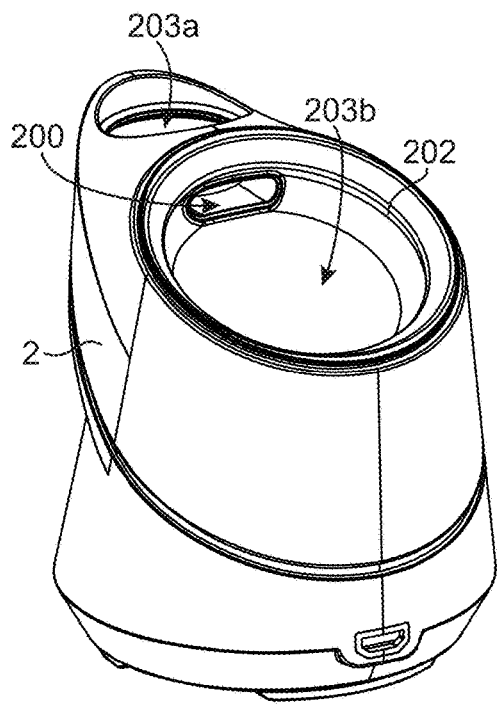
Figure 4D:
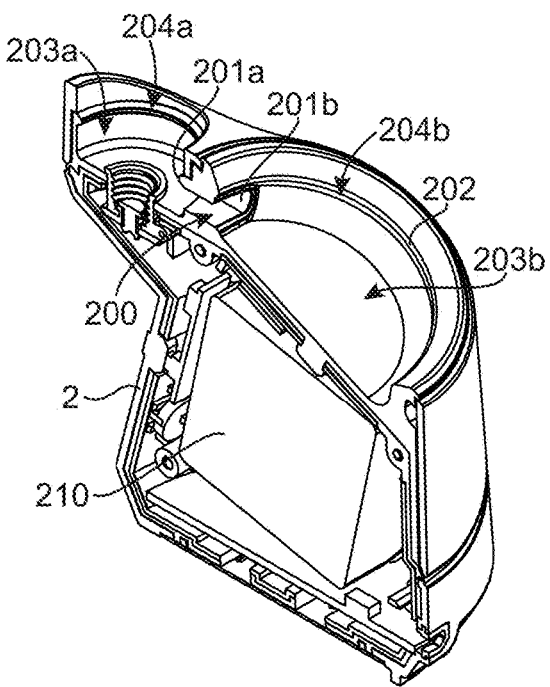

In one embodiment, referring to FIG. 12, the snap region 401 of the mouthpiece can comprises a fastening feature 202 comprising a circumferentially bulging protrusion 430 along a height of the snap region, where a diameter D of the protrusion 430 exceeds a minimum diameter $D_2$ of the recessed region of the base at some point along the height of the region (e.g., at a point where a sealing member 204b protrudes into the recessed region, see FIG. 4A). In certain embodiments, passing the bulging protrusion 430 past the minimum diameter $D_2$ of the recessed region causes the snap region to be removably retained in the recessed region. In one embodiment, the mouthpiece further comprises a fastening feature 202 comprising an annular indentation 432 formed about a circumference of the snap region portion of the mouthpiece. For example, the annular indentation may be configured to conformally mate with the circumferential sealing member 204b extending from a sidewall of the recessed region of the base, so as to form a seal therebetween. In one embodiment, the annular indentation can comprise an annular groove and/or annular channel formed in the mouthpiece housing at the snap region. In one embodiment, the annular indention may be located above the at least one mouthpiece gas inlet in the snap region, and/or the circumferentially bulging protrusion may have the at least one mouthpiece inlet formed therein. According to yet another embodiment, the fastening feature comprises a tapering snap region profile, the snap region having a first region adjacent the bottom of the mouthpiece housing (e.g., at the bulging protrusion) having a first diameter $D_1$, and a second region that is spaced apart from the first region (e.g. at the annular indentation) having a second diameter $D_3$, and wherein the diameter of the snap region decreases from the first region to the second region (e.g., D3 is less than D1).

In one embodiment, a method of using a portable electronic vaporizer as described according to any of the embodiments herein, can comprise loading vaporizable product into the container, optionally at least partially filling the mouthpiece with water in water filter regions thereof, activating the heating element to at least partially vaporize the product in the container, and inhaling gas exiting the mouthpiece inlet, the gas comprising ambient air having vaporize product and water vapor entrained therein.

What is claimed is:

1. A portable electronic vaporizing device comprising:
   a base having a gas flow path conduit therein and a housing for one or more components for electrically connecting to a power source and/or controlling the device, the gas flow path conduit comprising a conduit inlet and a conduit outlet;
   a mouthpiece that is removably attachable to the base, the mouthpiece comprising:
   a mouthpiece housing comprising one or more mouthpiece walls at least partly defining a mouthpiece internal flow path through the mouthpiece housing;
   an inhalation outlet formed in a region of the one or more mouthpiece walls; and
   at least one mouthpiece inlet capable of being placed in communication with the conduit outlet of the base upon attachment of the mouthpiece to the base, to receive a flow of gas into the mouthpiece from the base; and
   an atomizer that is removably attachable to the base, the atomizer comprising:
   an atomizer inlet configured to receive a flow of gas into the atomizer;
   an atomizer housing comprising one or more atomizer housing walls that at least partially define an atomizer internal flow path therein;
   a container within the atomizer housing that is capable of holding a vaporizable product,
   a heating element capable of heating the vaporizable product held in the container, the heating element being configured to be electrically connected to the one or more components for electrically connecting to the power source and/or controlling the device that are housed in the base;
   a first container inlet capable of introducing gas into the container to entrain vaporizable product;
   one or more second container outlets capable of flowing the gas having the vaporizable product entrained therein into atomizer internal flow path; and
   one or more atomizer outlets capable of receiving the flow of gas from the atomizer internal flow path, and providing the flow of gas to the conduit inlet of the base,
   wherein the flow of gas having the vaporizable product entrained therein flows from the atomizer internal flow path and through the gas flow conduit inlet of the base to the mouthpiece inlet, and along the mouthpiece internal flow path to the inhalation outlet.

2. The portable electronic vaporizing device according to claim 1, wherein the atomizer is removable from the base independently of removal of the mouthpiece.

3. The portable electronic vaporizing device according to claim 1, wherein the base comprises a first recessed receiving region formed therein that is configured to removably receive the atomizer, and a second recessed receiving region formed therein that is configured to removably receive the mouthpiece.

4. The portable electronic vaporizing device according to claim 3, wherein an airtight seal is formed between the between the base and the atomizer and/or between the base and the mouthpiece, in one or more of the first and second recessed receiving regions.

5. The portable electronic vaporizing device according to claim 3, wherein the base comprises one or more of (i) at least one conformal liner disposed in the first recessed receiving region that is configured to conformally receive at least a portion of the atomizer, and (ii) at least one conformal liner disposed in the second recessed receiving region that is configured to conformally receive at least a portion of the mouthpiece.

6. The portable electronic vaporizing device according to claim 5, wherein the base comprises the at least one conformal liner disposed in the second recessed receiving region that is configured to conformally receive an outer circumferential surface of a fastening region located at a lower portion of the mouthpiece.

7. The portable electronic vaporizing device according to claim 1, wherein the atomizer comprises a heating element disposed below a bottom surface of the container that adapted to receive the vaporizable product.

8. The portable electronic vaporizer device according to claim 1, wherein the one or more second container outlets in the atomizer that flow the gas having the vaporizable product entrained therein out of the container and into the atomizer internal flow path, are located towards a top end of the atomizer and radially externally to the first container inlet, and are positioned in an arrangement circumferentially surrounding the first container inlet.

9. The portable electronic vaporizing device according to claim 8, wherein the one or more second container outlets comprise one or more of:
   (i) one or more apertures formed in one or more walls located at an upper portion of the container;
   (ii) one or more apertures formed between a top surface of the container and an annular ring disposed above the container, the annular ring comprising one or more indentations formed in a bottom surface about a circumference thereof that form the one or more apertures between the bottom surface of the annular ring and the top surface of the container; and
   (iii) one or more apertures formed about a circumference of an annular ring disposed above the container.

10. The portable electronic vaporizer device according to claim 1, wherein the flow of gas through the atomizer comprises flow through the first container inlet into a top of the container, flow out of the container through the second container outlets that are separate from the inlet and disposed towards a top end of the atomizer, and wherein the atomizer housing at least partially directs gas from the one or more second container gas outlets along the internal atomizer gas flow path, in a passage formed between walls of the container and the atomizer housing, and wherein the atomizer housing comprises one or more apertures formed therein to flow gas from the internal atomizer gas flow path to an airtight passage that is external to the atomizer housing in a first recessed receiving region of the base.

11. The portable electronic vaporizer device according to claim 1, wherein the mouthpiece internal flow path comprises a convoluted flow path from the at least one mouthpiece inlet to the inhalation outlet, the mouthpiece comprising a first chamber that is internal to a second chamber that at least partially circumferentially surrounds the first chamber, and wherein the flow of gas along the mouthpiece internal flow path is received in the at least one mouthpiece inlet, passes through the first chamber and into the second chamber, and out of the inhalation outlet.

12. A method of using a portable electronic vaporizer according to claim 1, the method comprising:
   loading vaporizable product into the container;
   at least partially filling the mouthpiece with water in water filter regions thereof;
   activating the heating element to at least partially vaporize the product in the container; and
   inhaling gas exiting the mouthpiece inlet, the gas comprising ambient air having vaporize product and water vapor entrained therein.

13. A portable electronic vaporizing device comprising:
   a base having a gas flow path conduit therein and a housing for one or more components for electrically connecting to a power source and/or controlling the device, the gas flow path conduit comprising a conduit inlet and a conduit outlet;
   a mouthpiece that is removably attachable to the base, the mouthpiece comprising:
   a mouthpiece housing comprising one or more mouthpiece walls at least partly defining a mouthpiece internal flow path through the mouthpiece housing;
   an inhalation outlet formed in a region of the one or more mouthpiece walls; and
   at least one mouthpiece inlet capable of being placed in communication with the conduit outlet of the base upon attachment of the mouthpiece to the base, to receive a flow of gas into the mouthpiece from the base; and
   an atomizer that is removably attachable to the base, the atomizer comprising:
   an atomizer inlet configured to receive a flow of gas into the atomizer;
   an atomizer housing comprising one or more atomizer housing walls;
   a container within the atomizer housing that is capable of holding a vaporizable product;
   a heating element within the atomizer housing capable of heating the vaporizable product held in the container, the heating element being configured to be electrically connected to the one or more components for electrically connecting to the power source and/or controlling the device that are housed in the base;
   a container inlet capable of introducing gas into the container to entrain vaporizable product; and
   one or more container outlets capable of flowing the gas having the vaporizable product entrained therein out of the container,
   wherein the flow of gas having the vaporizable product entrained therein flows from the one or more container outlets and is received by the conduit inlet of the gas flow conduit of the base, flows through the gas flow conduit of the base to the conduit outlet and is received by the mouthpiece inlet, and flows along the mouthpiece internal flow path to the inhalation outlet.

* * * * *